United States Patent [19]

Heymés et al.

[11] 4,420,478

[45] Dec. 13, 1983

[54] NOVEL OXIMES

[75] Inventors: René Heymés, Romainville; André Lutz, Strasbourg, both of France

[73] Assignee: Roussel Uclaf, Paris, France

[21] Appl. No.: 28,372

[22] Filed: Apr. 9, 1979

[30] Foreign Application Priority Data

Apr. 14, 1978 [FR] France ................................. 78 11065
Oct. 5, 1978 [FR] France ................................. 78 28465

[51] Int. Cl.³ .................... A61K 31/545; C07D 501/46
[52] U.S. Cl. ......................................... 424/246; 544/22
[58] Field of Search ........................... 424/246; 544/22

[56] References Cited

U.S. PATENT DOCUMENTS 4,076,936 2/1978 Laundon .............................. 424/246
4,098,888 7/1978 Ochiai et al. .......................... 544/28

OTHER PUBLICATIONS

Bucourt et al., "C. R. Acad. Sc. Paris" May 1977, p. 1847ff.
Numata et al., The Journal of Antibiotics, vol. 31, No. 12, pp. 1262-1271, Dec. 1978.

*Primary Examiner*—Paul M. Coughlan, Jr.

*Attorney, Agent, or Firm*—Hammond & Littell, Weissenberger and Muserlian

[57] ABSTRACT

Novel syn isomers of oximes of 3-azidomethyl-7-aminothiazolyl-cephalosporanic acids of the formula

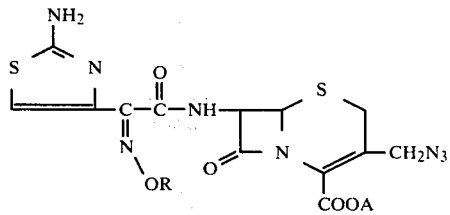

wherein R is selected from the group consisting of hydrogen, alkyl of 1 to 4 carbon atoms, unsaturated alkyl of 2 to 4 carbon atoms, benzoyl and —(CH$_2$)$_n$—R$_1$, n is an integer from 1 to 4, R$_1$ is selected from the group consisting of NH$_2$ and —COOA' and A' and A are selected from the group consisting of hydrogen, alkali metal, alkaline earth metal, magnesium, —NH$_4$, an easily cleavable ester group and a non-toxic, pharmaceutically acceptable organic amine and their non-toxic, pharmaceutically acceptable acid addition salts having antibiotic activity and a novel process and novel intermediates for their preparation.

24 Claims, No Drawings

NOVEL OXIMES

STATE OF THE ART

Related cephalosporanic compounds are described in French Pat. Nos. 2,137,899; 2,294,690; 2,348,218; 2,348,219; 2,255,076 and 2,355,849, Belgium Pat. No. 856,045 and copending commonly assigned U.S. Patent Applications Ser. Nos. 761,270 filed Jan. 21, 1977, 796,315 filed May 12, 1977 now abandoned in favor of continuation-in-part application Ser. No. 817,114 filed July 19, 1977 and now U.S. Pat. No. 4,152,432 and 886,421 filed Mar. 14, 1978.

OBJECTS OF THE INVENTION

It is an object of the invention to provide the novel oximes of formula I and their non-toxic, pharmaceutically acceptable acid addition salts and to a novel process and novel intermediates for their preparation.

It is another object of the invention to provide novel antibiotic compositions and to a novel method of treating bacterial infections in warm-blooded animals.

These and other objects and advantages of the invention will become obvious from the following detailed description.

THE INVENTION

The novel compounds of the invention are selected from the group consisting of syn isomers of oximes of 3-azidomethyl-7-amino-thiazolyl-acetamido-cephalosporanic acids of the formula

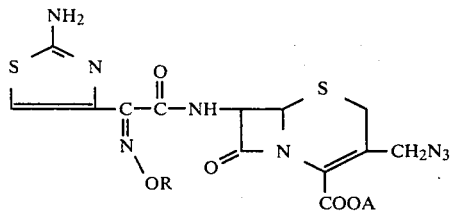

wherein R is selected from the group consisting of hydrogen, alkyl of 1 to 4 carbon atoms, unsaturated alkyl of 2 to 4 carbon atoms, benzoyl and —(CH$_2$)$_n$—R$_1$, n is an integer from 1 to 4, R$_1$ is selected from the group consisting of NH$_2$ and —COOA' and A' and A are selected from the group consisting of hydrogen, alkali metal, alkaline earth metal, magnesium, —NH$_4$, an easily cleavable ester group and a non-toxic, pharmaceutically acceptable organic amine and their non-toxic, pharmaceutically acceptable acid addition salts.

Examples of suitable groups for R are alkyls such as methyl, ethyl, propyl, isopropyl, butyl, sec.-butyl and tert.-butyl and alkenyl and alkynyl such as vinyl, allyl, ethynyl, propargyl, butenyl and butynyl, aminoalkyls such as aminomethyl, aminoethyl, aminopropyl and aminobutyl and carboxyalkyl such as carboxymethyl, carboxyethyl, carboxypropyl, carboxybutyl and salts or esters thereof.

Examples of groups of A and A' are alkali metals such as sodium, potassium and lithium, alkaline earth metals such as as calcium, magnesium, —NH$_4$, and organic amines such as methylamine, propylamine, trimethylamine, diethylamine, triethylamine, N,N-dimethylethanolamine, tris(hydroxymethyl)-aminomethane, ethanolamine, pyridine, picoline, dicyclohexylamine, morpholine, benzylamine, procaine, lysine, arginine, histidine and N-methylglucamine.

Examples of easily cleavable ester groups of A and A' are methoxymethyl, α-methylethyl, ethoxymethyl, isopropyloxymethyl, α-ethoxyethyl, methylthiomethyl, ethylthiomethyl, isopropylthiomethyl, pivaloyloxymethyl, acetoxymethyl, propionyloxymethyl, isobutyryloxymethyl, isovaleryloxymethyl, isovaleryloxyethyl, propionyloxyethyl, 1-acetoxyethyl, 1-acetoxypropyl, 1-acetoxybutyl, 1-acetoxyhexyl and 1-acetoxyheptyl.

Examples of suitable acids for the formation of the non-toxic, pharmaceutically acceptable acid addition salts are mineral acids like hydrochloric acid, hydrobromic acid, sulfuric acid and phosphoric acid and organic acids like acetic acid, maleic acid, trifluoroacetic acid, tartaric acid, methane sulfonic acid, benzene sulfonic acid and p-toluene sulfonic acid.

Among the preferred compounds of formula I are those wherein R is selected from the group consisting of hydrogen, alkyl of 1 to 4 carbon atoms, unsaturated alkyl of 2 to 4 carbon atoms, aminoethyl, benzoyl and carboxymethyl optionally salified or esterified and their non-toxic, pharmaceutically acceptable acid addition salts and especially those where R is hydrogen, alkyl of 1 to 4 carbon atoms and alkenyl and alkynyl of 2 to 4 carbon atoms and their acid addition salts.

Specific preferred compounds of formula I are the syn isomer of 3-azidomethyl-7-[2-(2-amino-4-thiazolyl)-2-hydroxyimino-acetamido]-ceph-3-eme-4-carboxylic acid, the syn isomer of 3-azidomethyl-7-[2-(2-amino-4-thiazolyl)-2-methoxyimino-acetamido]-ceph-3-eme-4-carboxylic acid and the syn isomer of 3-azidomethyl-7-[2-(2-amino-4-thiazolyl)-2-(2-aminoethoxyimino)-acetamido]-ceph-3-eme-4-carboxylic acid and their alkali metal, alkaline earth metal, magnesium, ammonium and organic amine salts and their easily cleavable ester and their non-toxic, pharmaceutically acceptable acid addition salts.

Specific preferred esters of formula I are the syn isomer of pivaloyloxymethyl 3-azidomethyl-7-[2-(2-amino-4-thiazolyl)-2-hydroxyimino-acetamido]-ceph-3-eme-4-carboxylate, the syn isomer of acetoxymethyl 3-azidomethyl-7-[2-(2-amino-4-thiazolyl)-2-hyroxyimino-acetamido]-ceph-3-eme-4-carboxylate and the syn isomer of 1-acetoxyethyl 3-azidomethyl-7-[2-(2-amino-4-thiazolyl)-2-hyroxyimino-acetamido]-ceph-3-eme-4-carboxylate.

The novel compounds of the invention may exist in the form of formula I or in the form of the formula

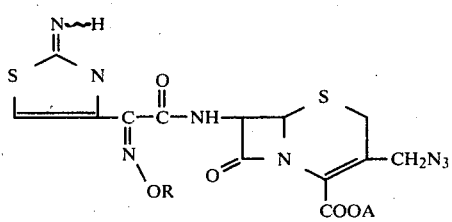

The novel process of the invention for the preparation of the compounds of formula I comprises reacting a compound of the formula

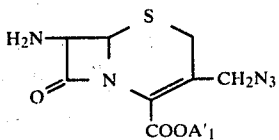

wherein $A_1'$ is selected from the group consisting of hydrogen and an easily removable ester group with an acid of the formula

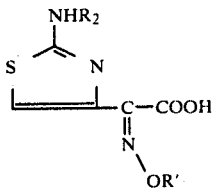

or a functional acid derivative thereof wherein $R_2$ is an amino protective group, $R'$ is selected from the group consisting of hydroxyl protective group, alkyl of 1 to 4 carbon atoms, alkenyl and alkynyl of 2 to 4 carbon atoms, benzoyl and —$(CH_2)_n$—$R_1'$, n is an integer from 1 to 4, $R_1'$ is selected from the group consisting of —COOA″ and —NH—$R_a$, A″ is an easily removable ester group and $R_a$ is an amino protective group to form the syn isomer of compound of the formula

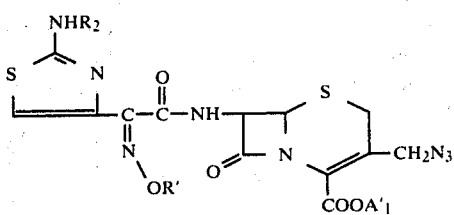

and treating the latter with at least one member of the group consisting of hydrolysis, hydrogenolysis agents and thiourea to obtain the syn isomer of a compound of the formula

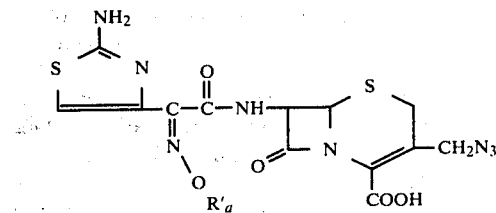

wherein $R_a'$ is selected from the group consisting of hydrogen, alkyl of 1 to 4 carbon atoms, alkenyl and alkynyl of 2 to 4 carbon atoms, benzoyl and —$(CH_2)_n$—$R_{1a}'$, $R_{1a}'$ is selected from the group consisting of —$NH_2$ and —COOH and n is an integer from 1 to 4 which is a compound of formula I wherein R is $R_a'$ and A is hydrogen and the compound of formula $I_a$ may be salified or esterified to obtain the other compounds of formula I.

Examples of easily removable ester groups of $A_1'$ and A″ are esters formed with easily removable groups such as esters of lower alkyls like butyl, isobutyl, tert.-butyl, pentyl and hexyl esters as well as acetoxymethyl, propionyloxymethyl, butyryloxymethyl, valeryloxymethyl, pivaloyloxymethyl, 2-acetoxyethyl, 2-propionyloxyethyl and 2-butyryloxyethyl esters. Examples of other esters are 2-mesylethyl, 2-iodoethyl, $\beta,\beta,\beta$-trichloro ethyl, vinyl, allyl, ethynyl, propynyl, benzyl, 4-methoxybenzyl, 4-nitrobenzyl, phenethyl, trityl, 3,4-dimethoxyphenyl and diphenylmethyl esters. Other esters are phenyl, 4-chlorophenyl, tolyl and tert.-butylphenyl esters.

The groups $R_2$ may be any of the normal amine protecting group but is preferably alkyl of 1 to 6 carbon atoms, especially tert.-butyl or tert.-amyl. Examples of other useful groups are acyls of an organic carboxylic acid of aliphatic carboxylic acids, aromatic carboxylic acids, heterocyclic carboxylic acids and carbamoyl groups. Examples of suitable acyl groups are lower alkanoyl such as acetyl, formyl, propionyl, butyryl, isobutyryl, valeryl, isovaleryl, oxalyl, succinyl and pivaloyl; lower alkoxycarbonyl and cycloalkoxycarbonyl such as methoxycarbonyl, ethoxycarbonyl, propoxycarbonyl, 1-cyclopropylethoxycarbonyl, isopropoxycarbonyl, butoxycarbonyl, tert-butoxycarbonyl, pentyloxycarbonyl, tert.-pentoxycarbonyl, hexyloxycarbonyl; benzoyl, toluolyl, naptholyl, phthaloyl, mesyl, phenylacetyl, phenylpropionyl; arylalkoxycarbonyl such as benzyloxycarbonyl. The acyl groups may be optionally substituted with at least one halogen such as chlorine, fluorine, bromine and iodine. Examples of such acyls are chloroacetyl, dichloroacetyl, trichloroacetyl, trifluoroacetyl and bromoacetyl.

Other examples of $R_2$ groups are arloweralkyl such as benzyl, 4-methoxybenzyl, phenethyl, trityl, 3,4-dimethoxybenzyl and benzhydryl; haloalkyl such as trichloroethyl; chlorobenzoyl, p-nitrobenzoyl, p-tert.-butylbenzoyl, phenoxyacetyl, caprylyl, n-decanoyl, acryloyl, methylcarbamoyl, phenylcarbamoyl, naphthylcarbamoyl as well as the corresponding thiocarbamoyls. The above list is not intended to be exhaustive as any amine protecting group known in peptide chemistry, for example, may be used.

The group $R_a$ is also selected from the above list.

The protective group for hydroxyl that $R'$ may be an acyl group such as acetyl, formyl, chloroacetyl, bromoacetyl, dichloroacetyl, trichloroacetyl, trifluoroacetyl, methoxyacetyl, phenoxyacetyl, benzoyl, benzoylformyl, p-nitrobenzoyl and other groups such as ethoxycarbonyl, methoxycarbonyl, propoxycarbonyl, carbonyl, tert.-butoxycarbonyl, 1-cyclopropylethoxycarbonyl, tetrahydropyranyl, tetrahydrothiopyranyl, methoxytetrahydropyranyl, trityl, benzyl, 4-methoxybenzyl, benzhydryl, trichloroethyl, 1-methyl-1-methoxy-ethyl and phthaloyl. Other acyl groups are propionyl, butyryl, isobutyryl, valeryl, isovaleryl, oxalyl, succinyl, pivaloyl, phenylacetyl, phenylpropionyl, mesyl, chlorobenzoyl, p-nitrobenzoyl, p-tert.butylbenzoyl, caprylyl, acryloyl, methylcarbamoyl, phenylcarbamoyl and naphthylcarbamoyl.

In a preferred mode of the process of the invention, the product of formula II is reacted with an acid functional derivative of formula III. The functional derivative may be the acid halide, mixed or symmetrical acid anhydride, or amide or an active ester. Examples of active esters are esters of 2,4-dinitrophenol and 1-hydroxybenzotriazole. The acid halide is preferably the acid chloride or acid bromide. Equally useful are the acid azide and acid amide. The anhydride may be formed in situ by reaction with a N,N′-disubstituted carbodiimide such as N,N′-dicyclohexylcarbodiimide.

Examples of mixed anhydride are those formed with isobutyl chloroformate and with pivaloyl chloride.

The acylation is preferably effected in at least one organic solvent such as methylene chloride although other solvents such as dimethylformamide, chloroform and tetrahydrofuran may be used.

When the acid halide is used, a molecule of hydrogen halide is freed in the reaction and preferably the reaction is effected in the presence of a base such as sodium hydroxide, potassium hydroxide, sodium carbonate, sodium bicarbonate, potassium carbonate, potassium bicarbonate, sodium acetate, triethylamine, pyridine, morpholine or N-methylmorpholine. The temperature is generally equal to or lower than room temperature.

The transformation of a compound of formula IV into a compound of formula $I_a$ is effected by removal of the amine protecting group $R_2$ as well as one or more of the groups $A_1'$, $A''$ and $R_a$. The removal of the $R_2$ is effected by acidic or basic hydrolysis or with hydrazine.

Acid hydrolysis is preferred for removing $R_2$ when it is alkoxycarbonyl or cycloalkoxycarbonyl optionally substituted such as tert.-pentyloxycarbonyl or tert.-butoxycarbonyl or optionally substituted aralkoxycarbonyl such as benzyloxycarbonyl, trityl, benzhydryle, tert.-butyl or 4-methoxybenzyl. The acid for the acid hydrolysis may be hydrochloric acid, benzene sulfonic acid, p-toluene sulfonic acid, formic acid or trifluoroacetic acid but other mineral or organic acids may be used.

The basic hydrolysis is preferably used to remove acyl protective groups such as trifluoroacetyl. The preferred bases are mineral bases such as alkali metal hydroxides like sodium hydroxide or potassium hydroxide, magnesium hydroxide, barium carbonate or alkali metal carbonates or bicarbonates such as sodium carbonate, sodium bicarbonate, potassium carbonate and potassium bicarbonate. Also useful are sodium acetate or potassium acetate or other bases.

The hydrolysis with hydrazine is preferably used to remove protective groups such as phthaloyl. The zinc-acetic acid system may also be used to remove $R_2$ groups such as trichloroethyl.

The benzhydryl and benzyloxycarbonyl groups are preferably removed with hydrogen in the presence of a catalyst. Chloroacetyl is preferably removed with thiourea in a neutral or acid medium by the reaction of Masaki [J.A.C.S., Vol. 90 (1968), p. 4508]. Other known ways may be used to remove the amine protecting group.

The preferred protecting groups are formyl, acetyl, ethoxycarbonyl, mesyl, trifluoroacetyl, chloroacetyl, and trityl. The preferred acids are formic acid and trifluoroacetic acid. The same conditions may be used to remove $A''$ and $R_a$.

Acid hydrolysis is preferably used for the removal of optionally substituted alkyl and aralkyl groups. The acid is preferably hydrochloric acid, formic acid, trifluoroacetic acid or p-toluene sulfonic acid. The other values for $R_a$, $A''$ and $A_1'$ can be removed by known processes. The process is preferably effected under moderate conditions such as at room temperature or with slight heating.

Naturally, when $R_2$ and $A_1'$ or $A''$ or $R_2$ for example, are of different types of groups to be removed, the products of formula IV may be treated with more than one of the agents recited above.

The products of formula I may be salified by known methods by treating the acids or a solvate thereof (such as ethanol solvate) or a hydrate thereof with a mineral base such as sodium hydroxide, potassium hydroxide, sodium bicarbonate, potassium bicarbonate, sodium carbonate or potassium carbonate or with salts of organic acid or mineral acid such as trisodiumphosphate.

Examples of salts of organic acids are sodium salts of saturated or unsaturated straight or branched chain aliphatic carboxylic acids of 1 to 18 carbon atoms, preferably 2 to 10 carbon atoms, and the aliphatic group may be interrupted with at least one heteroatom such as oxygen or sulfur or substituted with aryl radicals such as phenyl, thienyl, or furyl or with at least one hydroxyl or with at least one halogen such as fluorine, bromine or chlorine, preferably chlorine, or at least one carboxylic group or lower alkoxy carbonyl, preferably methoxy, ethoxy or propoxy or at least one aryloxy, preferably phenoxy. One can also use as the salts of organic acid the sufficiently soluble aromatic acids such as substituted benzoic acids where the preferred substituent is lower alkyl. Lower alkyl is intended to mean 1 to 6 carbon atoms in the description.

Examples of specific organic acids which are useful in their salt form are formic acid, acetic acid, acrylic acid, butyric acid, adipic acid, isobutyric acid, n-caproic acid, isocaproic acid, chloropropionic acid, crotonic acid, phenylacetic acid, 2-thienylacetic acid, 3-thienylacetic acid, 4-ethylphenylacetic acid, glutaric acid, monoethyl adipate, hexanoic acids, heptanoic acids, decanoic acids, oleic acid, stearic acid, palmitic acid, 3-hydroxypropionic acid, 3-methoxypropionic acid, 3-methylthiobutyric acid, 4-chlorobutyric acid, 4-phenylbutyric acid, 3-phenoxybutyric acid, 4-ethylbenzoic acid and 1-propylbenzoic acid. Especially preferred are sodium acetate, sodium 2-ethylhexanoate and sodium diethylacetate.

The salification may be effected with an organic base such as triethylamine, diethylamine, trimethylamine, propylamine, N,N-dimethylethanolamine, tris(hydroxymethyl) aminomethane as well as arginine, methylamine, ethanolamine, lysine pyridine, picoline, dicyclohexylamine, procaine, histidine, N-methylglucamine, morpholine and benzylamine.

The salification is preferably effected in at least one solvent such as water, ether, methanol, ethanol or acetone. The salts may be in amorphous or crystalline form depending on the reaction conditions. The crystalline salts are preferably formed by reacting the free acids of formula I with the salts of the above aliphatic carboxylic acids, especially sodium acetate.

The acids themselves are able to be obtained in the crystalline form such as crystallizing the acids from the sodium salts by dissolving the sodium salt in an aqueous alkanol such as methanol or ethanol and adding to the solution an organic acid such as formic acid or acetic acid or a mineral acid such as hydrochloric acid or sulfuric acid.

The esterification of the compounds of formula I may be effected by classical methods such as reacting the acid of formula $I_a$ with a derivative of the formula Z-Re wherein Z is selected from the group consisting of —OH and halogen such as chlorine, bromine, iodine and fluorine and Re is the desired ester moiety as indicated above.

The preferred process of the invention to form a compound of formula I wherein R is hydrogen, alkyl of 1 to 4 carbon atoms or alkenyl or alkynyl of 2 to 4 carbon atoms comprises reacting a compound of formula III wherein R' is a protective hydroxyl group or alkyl of 1 to 4 carbon atoms or alkenyl or alkynyl of 2 to 4 carbon atoms.

Another process of the invention for the preparation of a compound of formula I wherein R is hydrogen comprises reacting a compound of formula II with a compound of the formula

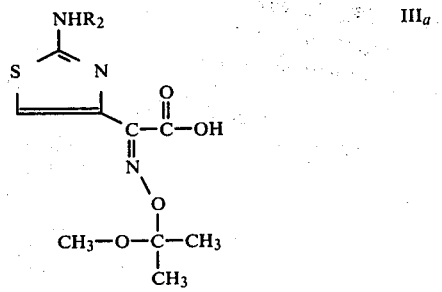

or an acid functional derivative thereof wherin R₂ has the above definition to obtain a compound of the formula

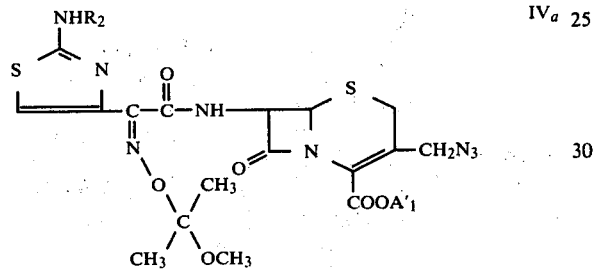

and when A₁' is hydrogen, the compound may be salified or esterified and the compound of formula IVa or its salt may be treated with an aqueous mineral acid to obtain a compound of the formula

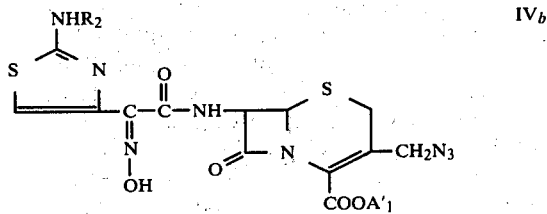

which is reacted with a carboxylic acid, a hydrogenolysis agent or thiourea or 2 of said agents depending on the values of R₂ and A₁' to obtain the compound of formula Ia wherein Rₐ' is hydrogen or reacting a compound of formula IVₐ with an acid and depending upon the values of R₂ and A₁' with a hydrogenolysis agent or thiourea or both to obtain a compound of formula Ia wherein Rₐ' is hydrogen which may be esterified or salified by known processes.

The reaction of compounds of formulae II and IIIₐ is effected under the conditions described previously and R₂ has the above definition. The optional salification and esterification can be effected under the usual conditions such as reaction with diazodiphenylmethane.

The aqueous mineral acid used to treat the compound of formula IVₐ is preferably aqueous hydrochloric acid such as N or 2 N hydrochloric acid with treatment at room temperature for ½ to several hours and the pH is then made neutral by addition of a base such as sodium bicarbonate.

When an acid is used to transform a compound of formula IVᵦ into a compound of formula Iₐ, an aqueous organic acid is preferably used and especially aqueous formic acid.

The acid used to transform directly a compond of formula IVₐ into a compound of formula Iₐ is preferably aqueous and is effected at a temperature greater than room temperature and probably about 50° C. with aqueous formic acid. The salification of compounds of formula Iₐ may be effected by known procedures.

Another process of the invention for the preparation of a compound of formula I comprises reacting the syn isomers of a compound of the formula

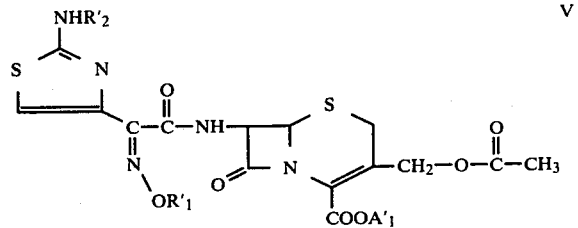

wherein R₂' is selected from the group consisting of hydrogen and an amino protective group, A₁' is selected from the group consisting of hydrogen and an easily cleavable ester group and R₁' is selected from the group consisting of hydrogen, hydroxyl protective group, alkyl of 1 to 4 carbon atoms, alkenyl and alkynyl of 2 to 4 carbon atoms, benzoyl and —(CH₂)ₙ—R₁'', n is an integer from 1 to 4, R₁'' is selected from the group consisting of —NH—Rₐ'' and —COOA₁''', Rₐ'' is selected from the group consisting of hydrogen and an amino protective group and A₁'' is selected from the group consisting of hydrogen and an easily cleavable ester group with an azide to obtain the syn isomer of a compound of the formula

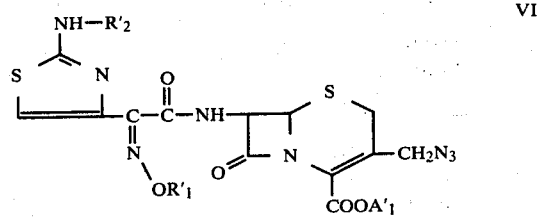

which when R₂' and A₁' are hydrogen, and R₁' is hydrogen, alkyl of 1 to 4 carbon atoms, alkenyl or alkynyl of 2 to 4 carbon atoms, benzoyl or —(CH₂)ₙ—R₁'' and R₁'' is —NH₂ or —COOH are compounds of formula Iₐ and the compounds of formula VI may be treated with at least one member of the group consisting of hydrolysis, hydrogenolysis agents and thiourea when R₂' is an amino protective group or A' is an easily removable ester group or R₁' is hydroxyl protective group or COOA₁'' and A₁'' is an easily removable ester group or —NHRₐ''' and Rₐ'' is an amino protective group to obtain the compounds of formula Iₐ wherein Rₐ' is hydrogen or —(CH₂)ₙ—R₁ₐ' and R₁ₐ' has the above definition and the resulting product may be esterified or salified to obtain the other compounds of formula I.

The amino protective groups of R₂', R₁' and Rₐ'' as well as the easily cleavable ester groups of A₁' and A₁'' may be selected from the groups discussed above. The azide to be reacted with the compound of formula V is preferably sodium azide but other alkali metal azides such as potassium azide may be used. Also useful are azides of organic bases such as the azide of tetramethylguanidine or ammonium azide formed in situ by reaction of ammonium chloride and sodium azide. The azide reaction is preferably effected in water or dimethylformamide but ethanol may also be used.

The removal of the protective groups for the compounds of formula VI as well as the optional salification and esterification of compounds of formula I$_a$ may be effected under the reaction conditions discussed above.

The antibiotic compositions of the invention are comprised of an antibiotically effective amount of at least one compound of formula I and its non-toxic, pharmaceutically acceptable acid addition salts and an inert pharmaceutical carrier. The compositions may be in the form of tablets, dragees, gelules, granules, suppositories, injectable solutions or suspensions, creams, pomades, gels, etc. prepared in the usual fashion.

Examples of suitable excipients or pharmaceutical carriers are talc, arabic gum, lactose, starch, magnesium stearate, cacao butter, aqueous or non-aqueous vehicles, fatty bodies of vegetable or animal origin, paraffinic derivatives, glycols, preservatives, diverse wetting agents, dispersants and emulsifiers. These compositions may be especially in the form of a powder intended to be dissolved extemporaneously in an appropriate vehicle, for example apyrogenetic sterile water. The compositions of the invention possess very good antibiotic activity against gram positive bacteria such as staphylococcus, streptococcus, particularly penicillin resistant staphylococcus as well as against gram negative bacteria such as coliform bacteria, Klebsiella, Salmonella and Proteus.

The compositions are therefore useful in the treatment of germ sensitive infections and particularly those of staphylococcia such as staphylococcal septicemia, staphylococcia malignant on the face or skin, pyodermatitis, septic or suppurantes sores, anthrax, phelgmons, eresipels, acute primitive or post-grip staphylococcia, bronchopneumonia or pulmonary suppurations. They are equally useful for the treatment of collibacillosis and associated infections, infections of Proteus, Klebsiella and Salmonella and other infections caused by gram negative bacteria.

The preferred compositions of the invention contain as the active ingredient at least one member of the group consisting of the syn isomer of 3-azidomethyl-7-[2-(2-amino-4-thiazolyl)-2-hydroxyimino-acetamido]-ceph-3-eme-4-carboxylic acid, the syn isomer of 3-azidomethyl-7-[2-(2-amino-4-thiazolyl)-2-methoxyimino-acetamido]-ceph-3-eme-4-carboxylic acid and the syn isomer of 3-azidomethyl-7-[2-(2-amino-4-thiazolyl)-2-(2-aminoethoxyimino)-acetamido]-ceph-3-eme-4-carboxylic acid and their alkali metal, alkaline earth metal, magnesium, ammonium and organic amine salts and their easily cleavable esters and their non-toxic, pharmaceutically acceptable acid addition salts.

Among the preferred compositions of the invention are the esters which include the syn isomer of pivaloyloxymethyl 3-azidomethyl-7-[2-(2-amino-4-thiazolyl)-2-hydroxyiminoacetamido]-ceph-3-eme-4-carboxylate, the syn isomer of acetoxymethyl 3-azidomethyl-7-[2-(2-amino-4-thiazolyl)-2-hydroxyimino-acetamido]-ceph-3-eme-4-carboxylate and the syn isomer of 1-acetoxyethyl 3-azidomethyl-7-[2-(2-amino-4-thiazolyl)-2-hydroxyimino-acetamido]-ceph-3-eme-4-carboxylate.

The novel method of the invention for combatting bacterial infections in warm-blooded animals, including humans, comprises administering to warm-blooded animals an antibacterially effective amount of at least one compound of formula I and its non-toxic, pharmaceutically acceptable acid addition salts. The compounds may be administered orally, rectally, parenterally or locally by topical application to the skin or mucous. The usual daily dose is 5 to 80 mg/kg depending on the specific compound and the method of administration. The compositions are also useful for sterilizing medical instruments.

The novel intermediate compounds of the invention are the syn isomers of compounds of the formula

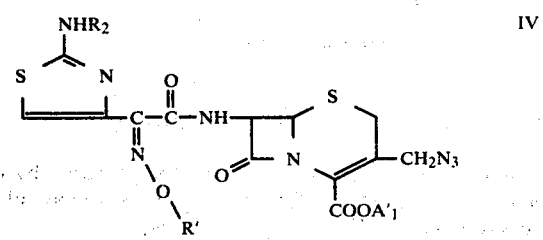

wherein $A_1'$, $R_2$ and $R'$ have the above definitions, especially the compounds wherein $R'$ is a hydroxyl protective group, alkyl of 1 to 4 carbon atoms or alkenyl or alkynyl of 2 to 4 carbon atoms and the syn isomers of compounds of the formula

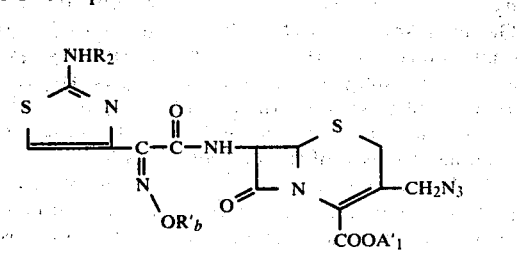

wherein $R_b'$ is selected from the group consisting of hydrogen and 1-methyl-1-methoxy-ethyl and $R_2$ and $A_1'$ have the above definitions.

The compounds of formula II wherein $A'$ is an easily removable ester group are prepared by the usual manner starting from 3-azidomethyl-7-amino-cehalosporanic acid.

The compounds of formula III wherein $R'$ is hydroxyl protective group, alkyl of 1 to 4 carbon atoms or alkeny or alkynyl of 2 to 4 carbon atoms are described in German Patent Application Ser. No. 27 02 501. The products of formula III wherein $R'$ is $-(CH_2)_n-R_1'$ and $R_1'$ is $-COOA''$ and $A''$ is an easily removable ester group may be prepared by reacting a compound of the formula

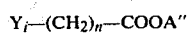

$Y_i-(CH_2)_n-COOA''$ wherein $Y_i$ is halogen or sulfate or sulfonate in the presence of a base with a syn isomer of a compound of the formula

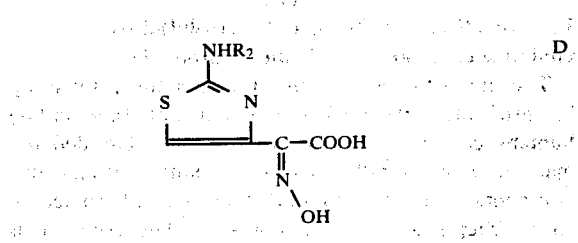

Product D is described as well in German patent application No. 27 02 501.

The compounds of formula III wherein R' is —(CH$_2$)$_n$—R$_1$' and R$_1$' is —NHR$_a$ and R$_a$ has the above definition may be prepared by reacting a compound of the formula NH$_2$R$_a$ with a compound of the formula

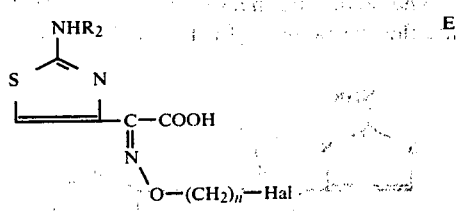

The compounds of formula E may be prepared by reacting a compound of formula D with a compound of formula Hal—(CH$_2$)$_n$—Hal.

The compounds of formula III wherein R' is benzoyl may be prepared by reacting a compound of formula D in the presence of a base with benzoyl chloride. The compounds of formula III$_a$ may be prepared by reacting a compound of formula D with 2-methoxypropene. The compounds of formula V wherein R$_1$' is hydrogen, hydroxyl protective group or alkyl are described in German Application Ser. No. 27 02 501. The other compounds of formula V may be prepared by reacting a corresponding compound of formula III with 7-amino-cephalosporanic acid under the same conditions as the reaction of compounds II and III followed by an eventual removal of the protective group.

In the following examples there are described several preferred embodiments to illustrate the invention. However, it is to be understood that the invention is not intended to be limited to the specific embodiments.

EXAMPLE 1 syn isomer of 3-azidomethyl-7-[2-(2-amino-4-thiazolyl)-2-hydroxyimino-acetamido]-ceph-3-eme-4-carboxylic acid STEP A: syn isomer of 3-azidomethyl-7-[2-(2-tritylamino-4-thiazolyl)-2-(1-methyl-1-methoxyethoxyimino)-acetamido]-ceph-3-eme-4-carboxylic acid A mixture of 6.9 g of 2-(2-tritylamino-4-thiazolyl)-2-hydroxyimino-acetic acid and 42 ml of methylene chloride and 7 ml of 2-methoxypropene was stirred for 30 minutes at room temperature and was then evaporated to dryness. The residue was taken up in 42 ml of methylene chloride. 1.76 g of dicyclohexylcarbodiimide were added thereto and the mixture was stirred for 30 minutes at room temperature and was vacuum filtered to remove 1.386 g of dicyclohexylurea. The filtrate was added over 10 minutes with stirring to a solution of 2.04 g of 3-azidomethyl-7-amino-ceph-3-eme-4-carboxylic acid in 16 ml of methylene chloride and 2 ml of triethylamine and the mixture was stirred at room temperature for one hour. The mixture was washed with 20 ml of N hydrochloric acid and the decanted organic phase was evaporated to dryness. The residue was taken up in 20 ml of ethyl acetate and the mixture was stirred for 10 minutes and was vacuum filtered to recover 3.002 g of the starting acid. The filtrate was evaporated to a volume of 10 ml and 1 ml of diethylamine was added thereto. 100 ml of ether were added thereto and the mixture was vacuum filtered to obtain 3.65 g of raw product. The latter was added to 15 ml of ethyl acetate and the mixture was vacuum filtered to remove a small amount of diethylamine salt of the starting acid. Ether was added to the filtrate and the mixture was vacuum filtered to obtain 2.498 g of the syn isomer of 3-azidomethyl-7-[2-(2-tritylamino-4-thiazolyl)-2-(1-methyl-1-methoxyethoxyimino)-acetamido]-ceph-3-eme-4-carboxylic acid.

STEP B: syn isomer of 3-azidomethyl-7-[2-(2-tritylamino-4-thiazolyl)-2-hydroxyimino-acetamido]-ceph-3-eme-4-carboxylic acid A mixture of the product of Step A, 10 ml of acetone and 3.5 ml of 2 N hydrochloric acid was stirred at room temperature for 50 minutes and the acetone was evaporated. The mixture was extracted with ethyl acetate and the organic phase was washed with water, dried and evaporated to dryness. The residue was triturated with ether and was vacuum filtered to obtain 1.95 g of the syn isomer of 3-azidomethyl-7-[2-(2-tritylamino-4-thiazolyl)-2-hydroxyimino-acetamido]-ceph-3-eme-4-carboxylic acid.

STEP C: syn isomer of 3-azidomethyl-7-[2-(2-amino-4-thiazolyl)-2-hydroxyimino-acetamido]-ceph-3-eme-4-carboxylic acid A mixture of the product of Step B and 6 ml of 2-1 formic acid-water mixture was stirred at 45°–50° C. was stirred for 10 minutes and was diluted with 7 ml of water. The mixture was vacuum filtered and the filtrate was evaporated to dryness. The residue was added all at once to 10 ml of water and the mixture was triturated and vacuum filtered to obtain 0.95 g of the raw syn isomer of 3-azidomethyl-7-[2-(2-amino-4-thiazolyl)-2-hydroxyimino-acetamido]-ceph-3-eme-4-carboxylic acid.

EXAMPLE 2 syn isomer of sodium 3-azidomethyl-7-[2-(2-amino-4-thiazolyl)-2-hydroxyimino-acetamido]-ceph-3-eme-4-carboxylate The product of Example 1 was added to 3 ml of a molar solution of sodium acetate in methanol and the mixture was vacuum filtered to remove slight insolubles. 1 ml of ethanol was added to the filtrate and the mixture was vacuum filtered. 5 ml of ethanol were added to the filtrate and the mixture was vacuum filtered to obtain 0.4 g of the syn isomer of sodium 3-azidomethyl-7-[2-(2-amino-4-thiazolyl)-2-hydroxyimino-acetamido]-ceph-3-eme-4-carboxylate.

RMN Spectrum [(CD$_3$)$_2$SO]:

peak at 6.81 ppm (5-proton of thiazole).

EXAMPLE 3 syn isomer of
3-azidomethyl-7-[2-(2-amino-4-thiazolyl)-2-methoxyimino-acetamido]-ceph-3-eme-4-carboxylic acid 1 g of sodium nitride was added to a solution of 4.55 g of the syn isomer of 3-acetoxymethyl-7-[2-(2-amino-4-thiazolyl)-2-methoxyimino-acetamido]-ceph-3-eme-4-carboxylic acid, 60 ml of water and 1.75 g of dipotassium phosphate and the mixture was stirred for 2 hours at 70° C. Another 0.5 g of dipotassium phosphate was added after one hour and the mixture was acidified at 20° C. with 3 ml of formic acid. The mixture was vacuum filtered and the product was washed with water and dried to obtain 1.5 g of raw product. Sodium chloride was added to the filtrate to obtain another 0.6 g of product and the product was extracted 3 times with 10 ml of acetone containing 10% of water. The mixture was vacuum filtered each time to remove insoluble impurities. The filtrate was evaporated to dryness and the residue was empasted with water to obtain 1.6 g of the syn isomer of 3-azidomethyl-7-[2-(2-amino-4-thiazolyl)-2-methoxyiminoacetamido]-ceph-3-eme-4-carboxylic acid.

EXAMPLE 4 syn isomer of sodium
3-azidomethyl-7-[2-(2-amino-4-thiazolyl)-2-methoxyimino-acetamido]-ceph-3-eme-4-carboxylate A mixture of the product of Example 3 and 5 ml of a molar solution of sodium acetate in methanol was stirred and was vacuum filtered to recover a brown solid. The fltrate was added to 1 ml of ethanol and was vacuum filtered to remove a second insoluble. The solid phases were added to 5 ml of ethanol and the mixture was vacuum filtered. The filtrate was evaporated to dryness and the residue was taken up in a little ethanol to obtain a second crop which was added to 2 ml of methanol. 5 ml of ethanol were added thereto and the mixture was vacuum filtered. The filtrate was evaporated to dryness and the residue was triturated with a little absolute ethanol to obtain 0.4 g of the syn isomer of sodium 3-azidomethyl-7-[2-(2-amino-4-thiazolyl)-2-methoxyimino-acetamido]-ceph-3-eme-4-carboxylate.

analysis: $C_{14}H_{13}O_5N_8S_2$: molecular weight=460.44, Calculated: %S 13.92, Found 13.7.

RMN Spectrum [$(CH_3)_2SO$]:
peak at 6.73 ppm (5-proton of thiazole).
peak at 3.83 ppm (=N—O—$CH_3$).

EXAMPLE 5

Bis trifluoroacetate of syn isomer of
3-azidomethyl-7-[2-(2-amino-4-thiazolyl)-2-(2-aminoethoxyimino)-acetamido]-ceph-3-eme-4-carboxylic acid STEP A: syn isomer of ethyl
2-(2-bromoethoxyimino)-2-(2-tritylamino-4-thiazolyl)-acetate 4.14 g of potassium carbonate were added under an inert atmosphere over 3 minutes at room temperature to a mixture of 4.94 g of the syn isomer of ethyl 2-(2-tritylamino-4-thiazolyl)-2-hydroxyimino-acetate hydrochloride in 10 ml of dimethylformamide and the mixture was stirred for 20 minutes at 20° C. 8.65 ml of 1,2-bromoethane were added thereto and the mixture was stirred for 30 hours. The mixture was poured into a mixture of 100 ml of distilled water and 20 ml of methylene chloride. The decanted aqueous phase was extracted with methylene chloride and the combined organic phases were washed with distilled water. The wash water was extracted with methylene chloride and the organic phase was dried and vacuum filtered. The filter was rinsed and the filtrate was evaporated to dryness. The residue was chromatographed over silica gel and was eluted with benzene containing 5% of ether. The first fraction was crystalized from methanol by dissolving at 50° to 60° C. and vacuum filtration at 0°–5° C. to obtain 1.16 g of the syn isomer of ethyl 2-(2-bromoethoxyimino)-2-(2-tritylamino-4-thiazolyl)-acetate in the form of a white cream product melting at 117° C. The following homogenous fraction was 1.258 g.

RMN Spectrum (deuterochloroform):
peaks at 3.55 ppm (triplet—$CH_2Br$) J=7 Hz; 4.51 ppm (triplet—N—O—$CH_2$) J=6 Hz; at 6.55 ppm (singulet—5-proton of thiazole.

STEP B: syn isomer of ethyl
2-(2-iodoethoxyimino)-2-(2-tritylamino-4-thiazolyl)-acetate A mixture of 6 g of the product of Step A, 60 ml of methyl ethyl ketone and 2.141 g of sodium iodide was refluxed for 70 minutes and was evaporated to dryness under reduced pressure. The residue was added to 120 ml of methylene chloride and the mixture was washed 5 times with 40 ml of water. Each wash water was extracted with 2 ml of methylene chloride and the combined organic phases were dried and evaporated to dryness. The residue was added to ether and the mixture was evaporated to dryness under reduced pressure to obtain 6.22 g of the syn isomer of ethyl 2-(2-iodoethoxyimino)-2-(2-tritylamino-4-thiazolyl)-acetate melting at 110° C.

RMN Spectrum (deuterochloroform):
peak at 3.31 ppm (—$CH_2I$—triplet center) J=7 $H_z$; at 6.53 ppm (5-proton of thiazole).

STEP C: syn isomer of ethyl
2-(2-tritylamino-4-thiazolyl)-2-(2-tritylaminoethoxyimino)-acetate A mixture of 12.2 g of the product of Step B, 80 ml of anhydrous dimethylformamide and 12.4 ml of triethylamine was refluxed under an inert atmosphere for 5 hours and 6.2 g of triethylamine were added thereto. The mixture stood at 100° C. for 7 hours and after cooling to room temperature, the mixture was poured into 1600 ml of distilled water. The mixture was extracted 6 times with 250 ml of benzene and the combined organic phases were washed with water, with an aqueous saturated sodium bicarbonate solution and then with an aqueous saturated sodium chloride solution and was dried and evaporated to dryness. The 23.5 g of resin was chromatographed over silica gel and was eluted with a 95–5 benzene-ether mixture. The principal fraction was chromatographed over silica gel and was eluted with pure methylene chloride to obtain 3.6 g of the syn isomer of ethyl 2-(2-tritylamino-4-thiazolyl)-2-(2-tritylaminoethoxyimino)-acetate.

RMN Spectrum (deuterochloroform):
peak at 6.46 ppm (5-proton of thiazole); centered at 2.45 ppm (triplet—$CH_2$—NH—) J=5 Hz.

STEP D: syn isomer of 2-(2-tritylamino-4-thiazolyl)-2-(2-tritylaminoethoxyimino)-acetic acid 3 ml of N sodium hydroxide solution were added under nitrogen to a mixture of 2 g of the product of Step C in 10 ml of dioxane and 66 m of absolute ethanol and after 65 hours, the mixture was vacuum filtered. The recovered sodium salt was washed 3 times with 3.5 ml of a 1-6.6 dioxane-ethanol mixture to obtain 1.445 g of sodium salt. The filtrate was saponified under the same conditions to obtain another 0.440 g of sodium salt. The first 1.445 g of sodium salt were added to a mixture of 30 ml of water and 30 ml of chloroform and the mixture was vigorously stirred and adjusted to a pH of 2 by addition of N hydrochloric acid (about 1.9 ml). The decanted organic phase was washed 4 times with 10 ml of water until the wash water was neutral. Each wash fraction was extracted with 3 ml of chloroform and the combined organic phases were dried and evaporated to dryness. The white powder was empasted twice with 2 ml of dichloroethane and twice with 2 ml of isopropyl ether. The product was dried under a reduced pressure to obtain 1.202 g of the syn isomer of 2-(2-tritylamino-4-thiazolyl)-2-(2-tritylaminoethoxyimino)-acetic acid with a melting point of 176° C. (decomposition). The second fraction of 0.440 g of sodium salt was treated in the same fashion to obtain 0.325 g of the said acid melting at 176° C. (decomposition) for a total yield of 1.527 g.

RMN Spectrum (deuterochloroform):
peaks at 6.65 ppm (5-proton of thiazole); at 2.95 ppm ($CH_2$—N).

STEP E: benzhydryl 3-azidomethyl-7-amino-ceph-3-eme-4-carboxylate

A mixture of 3.5 g of diphenyldiazomethane, 5 g of anhydrous sodium sulfate, 16 ml of dry methylene chloride, 3 g of 3-azidomethyl-7-amino-ceph-3-eme-4-carboxylic acid and 4.5 ml of methanol was stirred for 4 days at room temperature and was vacuum filtered. The filtrate was washed 4 times with a total of 50 ml of a 20-7-2 ether-methylene chloride-methanol mixture and the filtrate was evaporated to dryness to obtain 4.93 g of a yellow solid. The solid was kneaded successively with 30, 20 and 20 ml of essence B (b.p.=65°-75° C.) and twice with 20 ml of cyclohexane. The mixture was evaporated to dryness to obtain 2.16 g of product which was stirred for one hour twice with a total of 140 ml of ethyl acetate. The mixture was vacuum filtered and the product was washed twice with ethyl acetate. The filtrate was evaporated to dryness to obtain 1.22 g of the benzhydryl 3-azidomethyl-7-amino-ceph-3-eme-4-carboxylate melting at 161° C.

STEP F: syn isomer of benzhydryl 3-azidomethyl-7-[2-(2-tritylamino-4-thiazolyl)-2-(2-tritylaminoethoxyimino)-acetamido]-ceph-3-eme-4-carboxylate A mixture of 2.15 g of the acid of Step D in 16 ml of methylene chloride free of methanol was added under argon to 3 ml of a solution of 1.4 ml of triethylamine in 10 ml of methylene chloride and 3 ml of a solution of 1.25 ml of pivaloyl chloride in 10 ml of methylene chloride were added thereto dropwise at −20° C. The mixture was held at −10° C. for 50 minutes and after the temperature rose 10° C., 1.26 g of the product of Step E were added thereto all at once. The mixture was held at room temperature for 3 hours and was then iced for 12 hours and was evaporated to dryness under reduced pressure. The resin residue was empasted 3 times with 40 ml of an 8-2 benzene-ethyl acetate mixture and the combined filtrate was evaporated to dryness under reduced pressure. The residue was chromatographed over silica gel and was eluted with an 8-2 benzene-ethyl acetate mixture to obtain 1.81 g of the syn isomer of benzhydryl 3-azidomethyl-7-[2-(2-tritylamino-4-thiazolyl)-2-(2-tritylaminoethoxyimino)-acetamido]-ceph-3-eme-4-carboxylate.

U.V. Spectrum (0.1 N HCl in ethanol):
max. at 265 nm, $E_1^1 = 156$

IR Spectrum ($CHCl_3$):
absorption at 1793 $cm^{-1}$ ($\beta$-lactam); at 2105 $cm^{-1}$ ($N_3$); at 962 $cm^{-1}$ (>C=N—OR).

RMN Spectrum (deuterochloroform):
peak at 6.72 ppm (5-proton of thiazole).

STEP G: Bistrifluoroacetate of syn isomer of 3-azidomethyl-7-[2-(2-amino-4-thiazolyl)-2-(2-aminoethoxyimino)-acetamido]-ceph-3-eme-4-carboxylic acid A mixture of 0.76 g of the product of Step F and 8 ml of pure trifluoroacetic acid was stirred for 3 minutes at room temperature and was then cooled on an ice bath while 80 ml of an iced 1-1 isopropyl ether-ether mixture were added thereto. The mixture was vacuum filtered and the recovered product was washed with a 1-1 isopropyl ether-ether mixture and with isopropyl ether and dried under reduced pressure to obtain 300 mg of the trifluoroacetate of syn isomer of 3-azidomethyl-7-[2-(2-amino-4-thiazolyl)-2-(2-aminoethoxyimino)-acetamido]-ceph-3-eme-4-carboxylic acid melting at 190° C.

U.V. Spectrum (0.1 N HCl in ethanol):
Max. at 260 nm, $E_1^1 = 270$

I.R. Spectrum (Nujol):
absorption at 1774 $cm^{-1}$ ($\beta$-lactam); at 2104 $cm^{-1}$ ($N_3$).

RMN Spectrum [$(CD_3)_2SO$]:
peak at 6.83 ppm (5-proton of thiazole).

EXAMPLE 6 syn isomer of pivaloyloxymethyl 3-azidomethyl-7-[2-(2-amino-4-thiazolyl)-2-hydroxyimino-acetamido]-ceph-3-eme-4-carboxylate

STEP A: Iodomethyl pivalate

A mixture of 190 mg of chloromethyl pivalate, 225 mg of sodium iodide and 4 ml of acetone was refluxed for 40 minutes and was cooled to obtain a suspension of iodomethyl pivalate.

STEP B: syn isomer of pivaloyloxymethyl 3-azidomethyl-7-[2-(2-tritylamino-4-thiazolyl)-2-(1-methyl-1-methoxy-ethoxyimino)acetamido-]-ceph-3-eme-4-carboxylate A suspension of 739 mg of the syn isomer of 3-azidomethyl-7-[2-(2-tritylamino-4-thiazolyl)-2-(1-methyl-1-methoxyethoxyimino)-acetamido]-ceph-3-eme-4-carboxylic acid, 76 g of potassium carbonate and 3 ml of dimethylformamide was stirred for 10 minutes at 20° C. and after cooling the mixture to 0° to 5° C., the suspension of Step A was slowly added thereto. The mixture was stirred at 0° to 5° C. for 30 minutes and then at 20° C. for one hour and a mixture of 40 ml of water and 1.5 ml of N hydrochloric acid was added thereto. The mixture was vacuum filtered and the recovered product was washed with water and dried to obtain 850 mg of the syn isomer of pivaloyloxymethyl 3-azidomethyl-7-[2-(2-tritylamino-4-thiazolyl)-2-(1-methyl-1-methoxy-ethoxyimino)-acetamido]-ceph-3-eme-4-carboxylate.

STEP C: Pivaloyloxymethyl 3-azidomethyl-7-[2-(2-amino-4-thiazolyl)-2-hydroxyimino-acetamido]-ceph-3-eme-4-carboxylate A mixture of 753 mg of the product of Step B, 0.75 ml of 98% formic acid and 9.25 ml of 50% aqueous formic acid was stirred at 55°–60° C. for 12 minutes and the mixture was evaporated to dryness at a temperature not above 30° C. The residue was taken up in 5 ml of water and the mixture was vacuum filtered. The product was washed with water and then with isopropyl ether and dried. The 481 mg of product was chromatographed over silica gel and was eluted with a 1-1 acetone-methylene chloride mixture to obtain 211 mg of the pivaloyloxymethyl 3-azidomethyl-7-[2-(2-amino-4-thiazolyl)-2-hydroxyimino-acetamido]-ceph-3-eme-4-carboxylate.

I.R. Spectrum (chloroform):
absorption at 1791 cm$^{-1}$ (C=O of β-lactam); at 1753 cm$^{-1}$

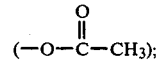
(—O—C—O—C— ester);

at 1675 cm$^{-1}$ (amide); at 1654–1636 cm$^{-1}$ (C=C and conjugated C=N); at 1609–1483 cm$^{-1}$ (aromatic-deformation of NH$_2$).

RMN Spectrum (deuterochloroform):
peaks at 1.22 ppm (tert.-butyl); at 3.52 ppm (CH$_2$—S); at 3.9 to 4.15 ppm and 4.26 to 4.5 ppm (—CH$_2$N$_3$); at 5 to 5.08 ppm (6-proton); at 6.92 ppm (5-proton of thiazole-syn isomer).

EXAMPLE 7 syn isomer of acetoxymethyl 3-azidomethyl-7-[2-(2-amino-4-thiazolyl)-2-hydroxyimino-acetamido]-ceph-3-eme-4-carboxylate STEP A: syn isomer of acetoxymethyl 3-azidomethyl-7-[2-(2-tritylamino-4-thiazolyl)-2-(1-methyl-1-methoxyethoxyimino)-acetamido]-ceph-3-eme-4-carboxylate A mixture of 141 mg of chloromethyl acetate, 225 mg of sodium iodide and 4 ml of acetone was refluxed for 40 minutes and was cooled to obtain a suspension of iodomethyl acetate. Using the procedure of Step B of Example 6, 739 mg of 3-azidomethyl-7-[2-(2-tritylamino-4-thiazolyl)-2-(1-methyl-1-methoxy-ethoxyimino)-acetamido]-ceph-3-eme-4-carboxylic acid and the said suspension were reacted to obtain 698 mg of the syn isomer of acetoxymethyl 3-azidomethyl-7-[2-(2-tritylamino-4-thiazolyl)-2-(1-methyl-1-methoxyethoxyimino)-acetamido]-ceph-3-eme-4-carboxylate.

STEP B: syn isomer of acetoxymethyl 3-azidomethyl-7-[2-(2-amino-4-thiazolyl)-2-hydroxyimino-acetamido]-ceph-3-eme-4-carboxylate Using the procedure of Step C of Example 6, 695 mg of the product of Step A were reacted and chromatographed to obtain 100 mg of the syn isomer of acetoxymethyl 3-azidomethyl-7-[2-(2-amino-4-thiazolyl)-2-hydroxyimino-acetamido]-ceph-3-eme-4-carboxylate.

I.R. Spectrum (CHCl$_3$):
General absorption region at OH/NH; absorption at 2105 cm$^{-1}$ (azide); at 1769 cm$^{-1}$ and shoulder at 1746 cm$^{-1}$ (carbonyl of β-lactam, ester-acetate); at 1671 cm$^{-1}$ (amide); at 1571 to 1521 cm$^{-1}$ (amide II+heterocycle).

RMN Spectrum (deuterochloroform):
peaks at 2.13 ppm

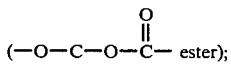
(—O—C—CH$_3$);

at 3.55 ppm (—CH$_2$—S—); at 3.92 to 4.15 ppm and 4.33 to 4.56 ppm (—CH$_2$—N$_3$); at 5.03 to 5.12 ppm (6-proton); at 5.91 ppm (—COOCH$_2$—OAc and 7-proton); at 7.03 ppm (5-proton of thiazole—syn isomer).

EXAMPLE 8 syn isomer of 1-acetoxyethyl 3-azidomethyl-7-[2-(2-amino-4-thiazolyl)-2-hydroxyimino-acetamido]-ceph-3-eme-4-carboxylate STEP A: syn isomer of 1-acetoxyethyl 3-azidomethyl-7-[2-(2-tritylamino-4-thiazolyl)-2-(1-methyl-1-methoxy-ethoxyimino)-acetamido]-ceph-3-eme-4-carboxylate A mixture of 739 mg of 3-azidomethyl-7-[2-(2-tritylamino-4-thiazolyl)-2-(1-methyl-1-methoxy-ethoxyimino)-acetamido]-ceph-3-eme-4-carboxylic acid, 76 mg of potassium carbonate and 3 ml of dimethylformamide was stirred at 20° C. for 10 minutes and after cooling the mixture to 0° to 50° C., 0.6 g of 1-bromoethyl acetate was slowly added thereto. The mixture was stirred for 20 minutes at 0° to 5° C. and for one hour at 20° C. and then a mixture of 40 ml of iced water and 1.5 ml of N hydrochloric acid were added thereto. The mixture was vacuum filtered and the product was rinsed with water and dried to obtain 761 mg of the syn isomer of 1-acetoxyethyl 3-azidomethyl-7-[2-(2-tritylamino-4-thiazolyl)-2-(1-methyl-1-methoxy-ethoxyimino)-acetamido]-ceph-3-eme-4-carboxylate.

STEP B: syn isomer of 1-acetoxymethyl 3-azidomethyl-7-[2-(2-amino-4-thiazolyl)-2-hydroxyimino-acetamido]-ceph-3-eme-4-carboxylate Using the procedure of Step C of Example 6, 760 mg of the product of Step A were reacted and chromatographed to obtain 98 mg of the syn isomer of 1-acetoxymethyl 3-azidomethyl-7-[2-(2-amino-4-thiazolyl)-2-hydroxyimino-acetamido]-ceph-3-eme-4-carboxylate.

I.R. Spectrum (CHCl$_3$):
general absorption region at OH/NH; at 2104 cm$^{-1}$ (azide); at 1793 and 1778 cm$^{-1}$ (carbonyl of lactam); at 1766 and 1740 cm$^{-1}$ (ester+OAc); at 1675 cm$^{-1}$ (amide); at 1609 cm$^{-1}$ (NH$_2$ deformation).

U.V. Spectrum (ethanol):
Max. at 222 nm, $E_1^1 = 319$, $\epsilon = 16,300$
Max. at 259 nm, $E_1^1 = 229$, $\epsilon = 11,700$ U.V. Spectrum (0.1 N HCl in ethanol):
Inflex. at 216 nm, $E_1^1 = 247$
Max. at 261 nm, $E_1^1 = 322$, $\epsilon = 16,400$ RMN Spectrum (deuterochloroform):
peaks at 1.5 to 1.58 ppm (CH$_3$—CH); at 2.08 ppm

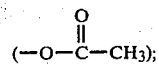

at 3.92 to 4.15 ppm and 4.33 to 4.56 ppm (—CH$_2$N$_3$); at 5.01 to 5.1 ppm (6-proton); at 5.87 to 5.95 ppm (7-proton); at 6.96 ppm (5-proton of thiazole-syn isomer).

EXAMPLE 9

Crystalline syn isomer of 3-azidomethyl-7-[2-(2-amino-4-thiazolyl)-2-hydroxyimino-acetamido]-ceph-3-eme-4-carboxylic acid 1 g of sodium salt of Example 2 was dissolved at 50° C. in 5 ml of a 1-1 ethanol-water mixture and 0.1 g of activated carbon was added thereto. The mixture was stirred and vacuum filtered and the filter was rinsed with 4 ml of a 1-1 ethanol-water mixture. 0.3 ml of 50% aqueous formic acid was added to the filtrate at 50° C. and after crystallization, the mixture was cooled and vacuum filtered. The product was rinsed with a 1-1 water-ethanol mixture and dried to obtain 574 mg of the crystalline syn isomer of 3-azidomethyl-7-[2-(2-amino-4-thiazolyl)-2-hydroxyimino-acetamido]-ceph-3-eme-4-carboxylic acid Analysis: Solvated with 0.5 ethanol, Calculated: %C 37.6, %H 3.4, %N 25.0, %S 14.3, Found: 37.7, 3.7, 23.9, 14.3.

EXAMPLE 10

Injectable solutions were prepared with 500 mg of either the syn isomer of sodium 3-azidomethyl-7-[2-(2-amino-4-thiazolyl)-2-hydroxyimino-acetamido]-ceph-3-eme-4-carboxylate or the syn isomer of sodium 3-azidomethyl-7-[2-(2-amino-4-thiazolyl)-2-methoxyimino-acetamido]-ceph-3-eme-4-carboxylate or the bistrifluoroacetate of the syn isomer of 3-azidomethyl-7-[2-(2-amino-4-thiazolyl)-2-(2-aminoethoxyimino)-acetamido]-ceph-3-eme-4-carboxylic acid and sufficient sterile aqueous excipient for a final volume of 5 ml.

Gelules were prepared with 250 mg of either the syn isomer of sodium 3-azidomethyl-7-[2-(2-amino-4-thiazolyl)-2-methoxyimino-acetamido]-ceph-3-eme-4-carboxylic acid or the syn isomer of 3-azidomethyl-7-[2-(2-amino-4-thiazolyl)-2-hydroxyimino-acetamido]-ceph-3-eme-4-carboxylic acid or the bistrifluoroacetate of the syn isomer of 3-azidomethyl-7-[2-(2-amino-4-thiazolyl)-2-(2-aminoethoxyimino)-acetamido]-ceph-3-eme-4-carboxylic acid and sufficient excipient for a final weight of 400 mg.

PHARMACOLOGICAL DATA

A. In Vitro Activity

The method used was a dilution of a liquid medium where a series of tubes received the same quantity of a sterile nutritive media and increasing doses of the test compounds were placed therein. Then each tube was seeded with a bacterial strain and was incubated for 24 or 48 hours at 37° C. in an oven. The increasing inhibition was determined by transillumination to determine the minimum inhibiting concentration (MIC in μg/ml) and the results are reported in the following Tables.

| STRAINS | M.I.C. in μg/ml 24 H | 48 H |
|---|---|---|
| PRODUCT OF EXAMPLE 2 | | |
| Staphylococcus aureus ATCC 6 538 Pen-Sensible | 0,2 | 0,2 |
| Staphylococcus aureus UC 1 123 Pen-Résistant | 0,2 | 0,2 |
| Staphylococcus aureus exp. n °54 146 | 0,2 | 0,3 |
| Streptococcus pyogènes A 561 | ≦0,02 | ≦0,02 |
| Streptococcus faecalis 5 432 | 3 | 5 |
| Streptococcus faecalis 99 F 74 | 10 | 20 |
| Bacillus subtilis ATCC 6 633 | 0,5 | 1 |
| Escherichia Coli Sensible Tétracycline ATCC 9 637 | 0,2 | 0,5 |
| Escherichia Coli Résistant Tétracycline ATCC 11 303 | 0,05 | 0,05 |
| Escherichia Coli Exp. TO$_{26}$B$_6$ | 0,05 | 0,1 |
| Escherichia Coli Résistant Gentamycine, Tobramycine R 55 123 D | 0,1 | 0,1 |
| Klebsiella pneumoniae Exp. 52 145 | 0,05 | 0,05 |
| Klebsiella pneumoniae 2 536 Résistant Gentamycine | 0,5 | 0,5 |
| Proteus mirabilis (indol—) A 235 | 0,1 | 0,1 |
| Salmonella typhimurium 420 | 0,1 | 0,1 |
| Enterobacter cloacae 681 | 10 | 10 |
| Providencia Du 48 | 3 | 5 |
| Serratia Résistant Gentamycine 2 532 | 5 | 5 |
| PRODUCT OF EXAMPLE 4 | | |
| Staphylococcus aureus ATCC 6 538 Pen-Sensible | 1 | 1 |
| Staphylococcus aureus UC 1 128 Pen-Résistant | 1 | 1 |
| Staphylococcus aureus exp. n °54 146 | 1 | 1 |
| Streptococcus pyogenes A 561 | ≦0,02 | ≦0,02 |
| Streptococcus faecalis 5 432 | 2 | 3 |
| Streptococcus faecalis 99 F 74 | 2 | 3 |
| Bacillus subtilis ATCC 6 633 | 1 | 2 |
| Escherichia Coli Sensible Tétracycline ATCC 9 637 | 0,2 | 0,2 |
| Escherichia Coli Resistant Tétracycline ATCC 9 303 | 0,5 | 0,5 |
| Escherichia Coli exp. TO$_{26}$B$_6$ | 0,2 | 0,2 |
| Escherichia Coli Résistant Gentamycine, Tobramycine R 55 123 D | 0,2 | 0,2 |
| Klebsiella pneumoniae Exp. 52 145 | ≦0,02 | ≦0,02 |
| Klebsiella pneumoniae 2 536 Résistant Gentamycine | 0,5 | 0,5 |
| Proteus mirabilis (indol—) A 235 | ≦0,02 | 0,05 |
| Salmonella typhimurium 420 | 0,1 | 0,1 |
| Enterobacter cloacae 681 | 20 | 40 |
| Providencia Du 48 | 3 | 5 |
| Serratia Résistant Gentamycine 2 532 | 0,5 | 0,5 |
| PRODUCT OF EXAMPLE 5 | | |
| Staphylococcus aureus ATCC 6 538 Pen-Sensible | 2 | 3 |
| Staphylococcus aureus UC 1 128 Pen-Résist. | 5 | 10 |
| Staphylococcus aureus exp. n °54 146 | 3 | 3 |
| Streptococcus pyogenes A 561 | ≦0,02 | ≦0,02 |
| Bacillus subtilis ATCC 6 633 | 0,5 | 0,5 |
| Escherichia Coli Sensible Tétracycline ATCC 9 637 | 0,5 | 0,5 |
| Escherichia Coli Résistant Tétracycline ATCC 11 303 | 0,05 | 0,05 |
| Escherichia Coli Exp. TO$_{26}$B$_6$ | 0,1 | 0,1 |
| Escherichia Coli Résistant Gentamycine Tobramycine R 55 123 D | 0,2 | 0,2 |
| Klebsiella pneumoniae Exp. 52 145 | 0,1 | 0,1 |
| Klebsiella pneumoniae 2 536 Résistant Gentamycine | 0,5 | 0,5 |
| Proteus mirabilis (indol—) A 235 | 0,1 | 0,2 |
| Proteus vulgaris (indol+) A 232 | 2 | 3 |
| Salmonella typhimurium 420 | 0,2 | 0,2 |
| Enterobacter cloacae 681 | 5 | 5 |
| Providencia Du 48 | 1 | 1 |
| Serratia Résistant Gentamycine 2 532 | 0,5 | 0,5 |

B. Experimental Infection

The activity of the compound of Example 4 was studied with an experimental infection of staphylococcus aureus 54,146 on groups of 10 mice given an intraperitoneal injection of a culture of the said strain for 24 hours in Antibiotic Medium No. 3 medium with a pH of 7 diluted to 1/6 with distilled water. The compound of Example 4 was subcutaneously administered one, 5 and 24 hours after the infection at the dosages indicated in the following Table. The number of dead mice was determined on the 8th day.

|  | Dose in mg | MORTALITY AFTER | | | | | | Mice surviving on the 8th day |
|---|---|---|---|---|---|---|---|---|
|  |  | 7 h | 21 h 30 | 23 h 15 | 28 h | 30 h | 48 h 30 | 6th day |  |
| Controls |  | 3 | 7 |  |  |  |  |  | 0/10 |
| Product of Example 4 | 0.05 |  | 7 | 1 | 2 |  |  |  | 0/10 |
| Product of Example 4 | 0.1 |  | 1 |  | 1 | 1 | 1 | 1 | 5/10 |
| Product of Example 4 | 0.25 |  |  |  |  |  |  |  | 10/10 |
| Product of Example 4 | 0.5 |  |  |  |  |  |  |  | 10/10 |

The results of the above Table show that in this test the compound of Example 4 exhibited excellent antibacterial activity.

Various modifications of the compounds and the methods of the invention may be made without departing from the spirit or scope thereof and it is to be understood that the invention is intended to be limited only as defined in the appended claims.

We claim:

1. A compound selected from the group consisting of syn isomers of oximes of 3-azidomethyl-7-aminothiazolyl-cephalosporanic acids of the formula

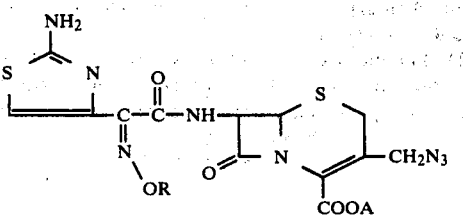

wherein R is selected from the group consisting of hydrogen, alkyl of 1 to 4 carbon atoms, alkenyl and alkynyl of 2 to 4 carbon atoms, benzoyl and $-(CH_2)_n-R_1$, n is an integer from 1 to 4, $R_1$ is selected from the group consisting of $NH_2$ and $-COOA'$ and $A'$ and $A$ are selected from the group consisting of hydrogen, alkali metal, alkaline earth metal, $-NH_4$, an easily cleavable ester group selected from the group consisting of methoxymethyl, α-methoxyethyl, ethoxymethyl, isopropyloxymethyl, α-ethoxyethyl, methylthiomethyl, ethylthiomethyl, isopropylthiomethyl, pivaloyloxymethyl, acetoxymethyl, propionyloxymethyl, isobutyryloxymethyl, isovaleryloxymethyl, isovaleryloxyethyl, propionyloxyethyl 1-acetoxyethyl, 1-acetoxypropyl, 1-acetoxybutyl, 1-acetoxyhexyl and 1-acetoxyheptyl and a non-toxic, pharmaceutically acceptable organic amine and their non-toxic, pharmaceutically acceptable acid addition salts.

2. A compound of claim 1 wherein R is selected from the group consisting of hydrogen, alkyl of 1 to 4 carbon atoms, alkenyl and alkynyl of 2 to 4 carbon atoms, aminoethyl, benzoyl and carboxymethyl optionally salified or esterified.

3. A compound of claim 1 wherein R is selected from the group consisting of hydrogen, alkyl of 1 to 4 carbon atoms and alkenyl and alkynyl of 2 to 4 carbon atoms.

4. A compound of claim 1 selected from the group consisting of the syn isomer of 3-azidomethyl-7-[2-(2-amino-4-thiazolyl)-2-hydroxyimino-acetamido]-ceph-3-eme-4-carboxylic acid and its alkali metal, alkaline earth metal, ammonium and organic amine salts and its easily cleavable esters and its non-toxic, pharmaceutically acceptable acid addition salts.

5. A compound of claim 1 selected from the group consisting of the syn isomer of 3-azidomethyl-7-[2-(2-amino-4-thiazolyl)-2-methoxyimino-acetamido]-ceph-3-eme-4-carboxylic acid and its alkali metal, alkaline earth metal, ammonium and organic amine salts and its easily cleavable esters and its non-toxic, pharmaceutically acceptable acid addition salts.

6. A compound of claim 1 selected from the group consisting of the syn isomer of 3-azidomethyl-7-[2-(2-amino-4-thiazolyl)-2-(2-aminoethoxyimino)-acetamido]-ceph-3-eme-4-carboxylic acid and its alkali metal, alkaline earth metal, ammonium and organic amine salts and its easily cleavable esters and its non-toxic, pharmaceutically acceptable acid addition salts.

7. A compound of claim 1 which is the crystalline form of the syn isomer of 3-azidomethyl-7-[2-(2-amino-4-thiazolyl)-2-hydroxyimino-acetamido]-ceph-3-eme-4-carboxylic acid.

8. A compound of claim 1 selected from the group consisting of the syn isomer of pivaloyloxymethyl 3-azidomethyl-7-[2-(2-amino-4-thiazolyl)-2-hydroxyimino-acetamido]-ceph-3-eme-4-carboxylate,the syn isomer of acetoxymethyl 3-azidomethyl-7-[2-(2-amino-4-thiazolyl)-2-hydroxyimino-acetamido]-ceph-3-eme-4-carboxylate and the syn isomer of 1-acetoxyethyl 3-azidomethyl-7-[2-(2-amino-4-thiazolyl)-2-hydroxyimino-acetamido]-ceph-3-eme-4-carboxylate.

9. An antibiotic composition comprising an antibiotically effective amount of at least one compound of claim 1 and an inert pharmaceutical carrier.

10. A composition of claim 9 wherein R is selected from the group consisting of hydrogen, alkyl of 1 to 4 carbon atoms, alkenyl and alkynyl of 2 to 4 carbon atoms, aminoethyl, benzoyl and carboxymethyl optionally salified or esterified.

11. A composition of claim 9 wherein R is selected from the group consisting of hydrogen, alkyl of 1 to 4 carbon atoms and alkenyl and alkynyl of 2 to 4 carbon atoms.

12. The composition of claim 9 wherein the compound is selected from the group consisting of the syn isomer of 3-azidomethyl-7-[2-(2-amino-4-thiazolyl)-2-hydroxyimino-acetamido]-ceph-3-eme-4-carboxylic acid and its alkali metal, alkaline earth metal, ammonium and organic amine salts and its easily cleavable esters and its non-toxic, pharmaceutically acceptable acid addition salts.

13. The composition of claim 9 wherein the compound is selected from the group consisting of the syn isomer of 3-azidomethyl-7-[2-(2-amino-4-thiazolyl)-2-methoxyimino-acetamido]-ceph-3-eme-4-carboxylic acid and its alkali metal, alkaline earth metal, ammonium and organic amine salts and its easily cleavable esters and its non-toxic, pharmaceutically acceptable acid addition salts.

14. The composition of claim 9 wherein the compound is selected from the group consisting of the syn isomer of 3-azidomethyl-7-[2-(2-amino-4-thiazolyl)-2-(2-aminoethoxyimino)-acetamido]-ceph-3-eme-4-carboxylic acid and its alkali metal, alkaline earth metal, ammonium and organic amine salts and its easily cleavable esters and its non-toxic, pharmaceutically acceptable acid addition salts.

15. The composition of claim 9 wherein the compound is selected from the group consisting of the syn isomer of pivaloyloxymethyl 3-azidomethyl-7-[2-(2-amino-4-thiazolyl)-2-hydroxyimino-acetamido]-ceph-3-eme-4-carboxylate, the syn isomer of acetoxymethyl 3-azidomethyl-7-[2-(2-amino-4-thiazolyl)-2-hydroxyimino-acetamido]-ceph-3-eme-4-carboxylate and the syn isomer of 1-acetoxyethyl 3-azidomethyl-7-[2-(2-amino-4-thiazolyl)-2-hydroxyimino-acetamido]-ceph-3-eme-4-carboxylate.

16. The composition of claim 9 wherein the compound is the crystalline form of the syn isomer of 3-azidomethyl-7-[2-(2-amino-4-thiazolyl)-2-hydroxyimino-acetamido]-ceph-3-4-carboxylic acid.

17. A method of treating bacterial infections in warm-blooded animals comprising administering to warm-blooded animals an antibiotically effective amount of at least one compound of claim 1.

18. The method of claim 17 wherein R is selected from the group consisting of hydrogen, alkyl of 1 to 4 carbon atoms, alkenyl and alkynyl of 2 to 4 carbon atoms, aminoethyl, benzoyl and carboxymethyl optionally salified or esterified.

19. The method of claim 17 wherein R is selected from the group consisting of hydrogen, alkyl of 1 to 4 carbon atoms and alkenyl and alkynyl of 2 to 4 carbon atoms.

20. The method of claim 17 wherein the compound is selected from the group consisting of the syn isomer of 3-azidomethyl-7-[2-(2-amino-4-thiazolyl)-2-hydroxyimino-acetamido]-ceph-3-eme-4-carboxylic acid and its alkali metal, alkaline earth metal, ammonium and organic amine salts and its easily cleavable esters and its non-toxic, pharmaceutically acceptable acid addition salts.

21. The method of claim 17 wherein the compound is selected from the group consisting of the syn isomer of 3-azidomethyl-7-[2-(2-amino-4-thiazolyl)-2-methoxyimino-acetamido]-ceph-3-eme-4-carboxylic acid and its alkali metal, alkaline earth metal, ammonium and organic amine salts and its easily cleavable esters and its non-toxic, pharmaceutically acceptable acid addition salts.

22. The method of claim 17 wherein the compound is selected from the group consisting of the syn isomer of 3-azidomethyl-7-[2-(2-amino-4-thiazolyl)-2-(2-aminoethoxyimino)-acetamido]-ceph-3-eme-4-carboxylic acid and its alkali metal, alkaline earth metal, ammonium and organic amine salts and its easily cleavable esters and its non-toxic, pharmaceutically acceptable acid addition salts.

23. The method of claim 17 wherein the compound is selected from the group consisting of the syn isomer of pivaloxymethyl 3-azidomethyl-7-[2-(2-amino-4-thiazolyl)-2-hydroxyimino-acetamido]-ceph-3-eme-4-carboxylate, the syn isomer of acetoxymethyl 3-azidomethyl-7-[2-(2-amino-4-thiazolyl)-2-hydroxyimino-acetamido]-ceph-3-eme-4-carboxylate and the syn isomer of 1-acetoxyethyl 3-azidomethyl-7-[2-(2-amino-4-thiazolyl)-2-hydroxyimino-acetamido]-ceph-3-eme-4-carboxylate.

24. The method of claim 17 wherein the compound is the crystalline form of the syn isomer of 3-azidomethyl-7-[2-(2-amino-4-thiazolyl)-2-hydroxyimino-acetamido]-ceph-3-eme-4-carboxylic acid.

* * * * *